(12) United States Patent
Che et al.

(10) Patent No.: US 7,026,480 B2
(45) Date of Patent: Apr. 11, 2006

(54) ORGANOMETALLIC LIGHT-EMITTING MATERIAL

(75) Inventors: Chi-Ming Che, Hong Kong (CN); Wei Lu, Hong Kong (CN); Michael Chi-Wang Chan, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 279 days.

(21) Appl. No.: 10/094,384

(22) Filed: Mar. 8, 2002

(65) Prior Publication Data

US 2002/0179885 A1 Dec. 5, 2002

Related U.S. Application Data

(60) Provisional application No. 60/274,142, filed on Mar. 8, 2001.

(51) Int. Cl.
  *C07F 17/02* (2006.01)
  *H01L 35/24* (2006.01)

(52) U.S. Cl. .............................. 546/4; 556/137; 257/40; 257/102; 313/504

(58) Field of Classification Search .................. 546/4; 556/137
  See application file for complete search history.

(56) References Cited

U.S. PATENT DOCUMENTS

| | | | |
|---|---|---|---|
| 6,048,630 A | | 4/2000 | Burrows et al. ............ 428/690 |
| 6,120,586 A | * | 9/2000 | Harada et al. ............. 106/1.25 |
| 6,150,545 A | * | 11/2000 | Harada et al. ............. 556/112 |
| 6,252,028 B1 | * | 6/2001 | Fehn et al. ................ 528/15 |
| 2004/0091738 A1 | * | 5/2004 | Psai et al. ................. 546/4 |

FOREIGN PATENT DOCUMENTS

| WO | WO 00/57676 | 9/2000 |
|---|---|---|
| WO | WO 01/41512 A1 | 6/2001 |

OTHER PUBLICATIONS

Malcolm H. Chisholm Inorg. CHem 16(9), 1977 pp 2177–2182.*
R. A. Bell, Inorg Chem 16(3) 1977 pp 677–686.*
Robert A. Bell Inorg Chem 16(3) 1977 pp 687–697.*
Sui–Wai Lai, et al, Inorganic Chem 38(18) pp 4046–4055 1999.*
Siu–Wai Lai, Organometallics pp 3327–3336, 1999.*
Raffaello Romeo, Inorganica Chimica Acta, vol. 265, Issues 1–2, Nov. 15, 1997, pp. 225–233.*
Yurngdong Jahng, Inorganica Chimica Acta, vol. 267, Issue 2, Jan. 10, 1998, pp. 265–270 □□.*
Chin Wing Chan, JACS, pp 11245–11253, 1993.*
Minghetti, Inorganic Chemistry 29(26) pp 5137–5138 (1990).*

C. W. Tang and S. A. VanSlyke, "Organic electroluminescent diodes", *Appl. Phys. Lett. 51* (12), Sep. 21, 1987, pp. 913–915.

(Continued)

*Primary Examiner*—Mark L. Berch
(74) *Attorney, Agent, or Firm*—Dickstein, Shapiro, Morin & Oshinsky, L.L.P.

(57) ABSTRACT

Disclosed herein are novel light-emitting materials of Formula I and II below. These new complexes are synthesized and found to be sufficiently stable to allow sublimation and vacuum deposition. These new emitters are electrophosphorescent and can be used in organic light-emitting devices (OLEDs) for device elements capable of emitting light of color ranging from orange to red with high-efficiency and high-brightness.

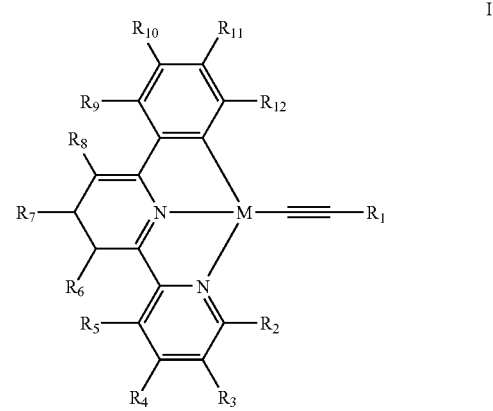

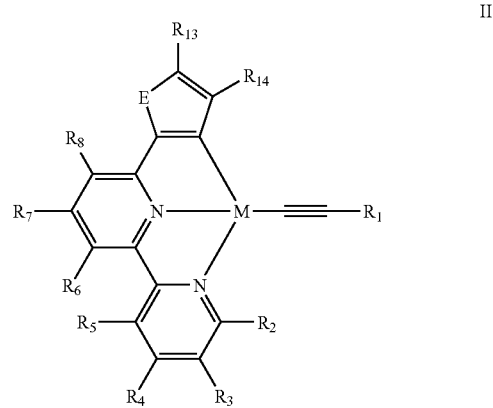

wherein E=Group 16 elements (including sulphur); M=Group 10 metal (including platinum); $R_1$–$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$ can also be selected from $(C{\equiv}C)_n R_{15}$, where $(C{\equiv}C)$ represents a carbon-carbon triple bond (acetylide group), n is selected from 1 to 10, and $R_{15}$ is selected from alkyl, aryl, substituted aryl, and tri(alkyl)silyl.

5 Claims, 10 Drawing Sheets

OTHER PUBLICATIONS

M. A. Baldo, D. F. O'Brien, Y. You, Shoustikov, S. Sibley, M. E. Thompson & S. R. Forrest, "Highly efficient phosphorescent emission from organic electroluminescent devices," *Nature*, vol. 395, Sep. 10, 1998, pp. 151–154.

Yuguang Ma, Houyu Zhang, Jiacong Shen, Chiming Che, "Electroluminescence from triplet metal–ligand charge–transfer excited state of transition metal complexes", *Synthetic Metals 94* (1998), pp. 245–248.

Chihaya Adachi, Marc. A. Baldo and Stephen R. Forrest, "High–efficiency organic electrophosphorescent devices with tris (2–phenylpyridine)iridium doped into electron–transporting materials", *Applied Physics Letters*, vol. 77, No. 6, Aug. 7, 2000, pp. 904–906.

Siu–Wai Lai, Michael Chi–Wang Chan, Tsz–Chun Cheung, Shie–Ming Peng and Chi–Ming Che, "Probing $d^8$–$d^8$ Interactions in Luminescent Mono– and Binuclear Cyclometalated Platinum(II) Complexes of 6–Phenyl–2,2'–bipyridines", *Inorg. Chem. 1999*, 38, pp. 4046–4055.

Tsz–Chun Cheung, Kung–Kai Cheung, Shie–Ming Peng and Chi–Ming Che, "Photoluminescent cyclometallated diplatinum(II,II) complexes: photophysical properties and crystal structures of PtL(PPh$_3$)ClO$_4$ and [Pt$_2$L$_2$(μ–dppm)][ClO$_4$]$_2$ (HL+6–phenyl–2,2'–bipyridine, dppm=Ph$_2$PCH$_2$PPh$_2$)", *J. Chem. Soc., Dalton Trans. 1996*, p. 1645–1651.

Siu–Wai Lai, Michael Chi–Wang Chan, Kung–Kai Cheung and Chi–Ming Che, "Carbene and Isocyanide Ligation at Luminescent Cyclometalated 6–Phenyl–2,2'–bipyridyl Platinum(II) Complexes: Structural and Spectroscopic Studies", *Organometallics 1999*, 18, pp. 3327–3336.

John H. K. Yip, Suwarno and Jagadese J. Vittal, "Syntheses and Electronic Spectroscopy of [PtL(L')][ClO$_4$]Complexes (HL=6–Phenyl–2,2'–bipyridine; L'=Pyridine, 4–Aminopyridine, 2–Aminopyridine, and 2,6–Diaminopyridine)", *Inorgan. Chem. 2000*, 39, 3537–3543.

Francesco Neve and Alessandra Crispini, Sebastiano Campagna, "Anisometric Cyclometalated Palladium(II) and Platinum(II) Complexes. Structural and Photophysical Studies", *Inorg. Chem 1997*, 36, pp. 6150–6156.

Fritz Kröhke. "The Specific Synthesis of Pyridines and Oligopyridines", *Synthesis*, Jan. 1976, pp. 1–24.

S. Takahashi, Y. Kuroyama, K. Sonogashira and N. Hagihara, , "A Convenient Synthesis of Ethylnylarenes and Di–ethynylarenes", Communications, *Synthesis*, Aug. 1980, pp. 627–630.

Edwin C. Constable, Roland P. G. Henney, Paul R. Raithby and Lynn R. Sousa, "Cyclometallation Reactions of 6–(2–Thienyl)–2,2'–bipyridine with $d^8$ Transition Metal Ions", *J. Chem. Soc. Dalton Trans. 1992*, pp. 2251–2258.

Edwin C. Constable, Roland P. G. Henney and Troy A. Leese, Derek A. Tocher, "Cyclometallation Reactions of 6–Phenyl–2,2'–bipyridine; a Potential C,N,N–DonorAnalogue of 2,2':6',2–Terpyridine, Crystal and Molecular Structure of Dichlorobis(6–phenyl–2–2'–bipyridine)ruthenium(II)", *J. Chem. Soc. Dalton Trans. 1990*, pp. 443–449.

Wei Lu, Boa–Xiu Mi, Michael C. W. Chan, Zheng Hui, Nianyong Zhu, Shuit–Tong Lee and Chi–Ming Che, "[CN-N)Pt(C≡C)$_n$R](HCNN=6–aryl–2,2'–bipyridine, n=1–4, R=aryl, SiMe$_3$) as a new class of light–emitting materials and their applications in electrophosphorescent devices", *Chemical Communications*, DOI: 10.1039/b108793b, 4 pages.

Vladimir V. Grushin, Norman Herron, Daniel D. LeCloux, William J. Marshall, Viacheslav A. Petrov and Ying Wang, "New, efficient electroluminescent materials based on organometallic Ir complexes", *Chem. Commun.*, 2001, pp. 1494–1495.

Hong Zhi Xie, Man Wah Liu, Oi Yan Wang, Xiao Hong Zhang, Chun Sing Lee, Liang Sun Hung, Shuit Tong Lee, Pang Fei Teng, Hoi Lun Kwong, Hui Zheng and Chi Min Che, "Reduction of Self–Quenching Effect in Organic Electrophosphorescence Emitting Devices via the Use of Sterically Hindered Spacers in Phosphorescence Molecules", *Advanced Materials* 2001, 13, No. 16, Aug. 16, pp. 1245–1248.

Sergey Lamansky, Peter Djurovich, Drew Murphy, Fears Abdel–Razzaq, Hae–Eun Lee, Chihaya Adachi, Paul E. Burrows, Stephen R. Forrest and Mark E. Thompson, "Highly Phosphorescent Bis–Cyclometalated Iridium Complexes: Synthesis, Photophysical Characterization, and Use in Organic Light Emitting Diodes", *J. Am. Chem. Soc.*, 2001 vol. 123, No. 18 , 4304–4312.

Chihaya Adachi, Marc. A. Baldo, Mark E. Thompson and Stephen R. Forrest, "Nearly 100% internal phosphorescence efficiency in an organic light emitting device", *Journal of Applied Physics*, vol. 90, No. 10, Nov. 15, 2001, pp. 5048–5051.

Chihaya Adachi, Raymond C. Kwong, Peter Djurovich, Vadim Adamovich, Marc. A. Baldo, Mark E. Thompson and Stephen R. Forrest, "Endothermic energy transfer: A mechanism for generating very efficient high–energy phosphorescent emission in organic materials", *Applied Physics Letters*, vol. 79, No. 13, Sep. 24, 2001, pp. 2082–2084.

Chihaya Adachi, Marc A. Baldo and Stephen R. Forrest, "High–efficiency red electrophosphorescence devices", *Applied Physics Letters*, vol. 78, No. 11, Mar. 12, 2001, pp. 1622–1624.

* cited by examiner

ORGANOMETALLIC LIGHT-EMITTING MATERIAL

RELATED APPLICATION

The subject application claims the priority of U.S. provisional patent application No. 60/274,142, filed on Mar. 8, 2001.

FIELD OF THE INVENTION

This invention relates to light-emitting materials which are discrete organometallic molecules in nature, which can be deposited as a thin layer by vacuum deposition, and which can act as electrophosphorescent emitters in high-efficiency and high-brightness organic light-emitting devices (OLEDs).

BACKGROUND OF THE INVENTION

Tang and coworkers first reported on high-performance organic light-emitting devices (OLEDs) in 1987 (Tang, C. W.; et al. *Appl. Phys. Lett.* 51, 913 (1987)). Their discovery was based on employing a multilayer structure containing an emitting layer and a hole transport layer of a suitable organic substrate. $Alq_3$ (q=deprotonated 8-hydroxyquinolinyl) was chosen as the emitting material and proven to be of high-performance because (1) it can form uniform thin films under 1000 Å using vacuum deposition, (2) it is a good charge carrier and (3) it exhibits strong fluorescence. Since then, there has been a flourish of research on OLEDs and materials used in these devices. Indeed, nearly every large chemical company in the world with optoelectronic interests has demonstrated some level of interest in OLEDs. Clearly, OLED technology is heading directly and rapidly into the marketplace. The attractiveness of OLEDs as it challenges traditional technologies such as cathode ray tubes (CRTs), liquid crystal displays (LCDs) and plasma displays is based on many features and advantages, including:

Low operating voltage,

Thin, monolithic structure,

Emits, rather than modulates light,

Good luminous efficiency,

Full color potential, and

High contrast and resolution.

OLED is a device built with organic semiconductors from which visible light can be emitted upon electrical stimulation. The basic heterostructure of an OLED is described in FIG. 1.

The layers may be formed by evaporation, spin-casting or chemical self-assembly. The thickness ranges from a few monolayers (self-assembled films) to about 1000 to 2000 Å. Such devices whose structure is based on the use of layers of organic optoelectronic materials generally rely on a common mechanism leading to optical emission, namely, the radiative recombination of a trapped charge. Under a DC bias, electrons are injected from a cathode (usually Ca, Al, Mg—Ag) and holes are injected from an anode (usually transparent indium tin oxide (ITO)) into the organic materials, where they travel in the applied field across the electron transporting layer (ETL) and the hole transporting layer (HTL) respectively until they meet, preferably on molecules in the emitting layer, and form a luminescent excited state (Frenkel exciton) which, under certain conditions, experiences radiative decay to give visible light. The electroluminescent material may be present in a separate emitting layer between the ETL and the HTL in what is referred as a multi-layer heterostructure. In some cases, buffer layers and/or other functional layers are also incorporated to improve the performance of the device. Alternatively, those OLEDs in which the electroluminescent emitters are the same materials that function either as the ETL or HTL are referred to as single-layer heterostructures.

In addition to emissive materials that are present as the predominant component in the charge carrier layers (HTL or ETL), other efficient luminescent material(s) may be present in relatively low concentrations as a dopant in these layers to realize color tuning and efficiency improvement. Whenever a dopant is present, the predominant material in the charge carrier layer may be referred to as a host. Ideally, materials that are present as hosts and dopant are matched so as to have a high level of energy transfer from the host to the dopant, and to yield emission with a relatively narrow band centered near selected spectral region with high-efficiency and high-brightness.

While fluorescent emitters with high luminescence efficiencies have been extensively applied as dopant in OLEDs, phosphorescent emitters have been neglected in this domain. However, the quantum efficiency of an electrofluorescence device is limited by the low theoretical ratio of singlet exciton (25%) compared to triplet exciton (75%) upon electron-hole recombination from electrical excitation. In contrast, when phosphorescent emitters are employed, the potentially high energy/electron transfer from the hosts to the phosphorescent emitters may result in significantly superior electroluminescent efficiency (Baldo, M. A.; et al. *Nature* 395, 151 (1998) and Ma, Y. G.; et al. *Synth. Met.* 94, 245 (1998)). Several phosphorescent OLED systems have been fabricated and have indeed proven to be of relative high-efficiency and high-brightness.

It is desirable for OLEDs to be fabricated using materials that provide electrophosphorescent emission corresponding to one of the three primary colors, i.e., red, green and blue so that they may be used as a component layer in full-color display devices. It is also desirable that such materials are capable of being deposited as thin films using vacuum deposition techniques, which has been prove to be a common method for high-performance OLED fabrication, so that the thickness of the emitting layer can be precisely controlled.

Presently, the highest efficiencies and brightness have been obtained with green electrophosphorescent devices (15.4±0.2% for external quantum efficiency and almost 100% for internal efficiency, $10^5$ $Cd/m^2$ for maximum luminance) using $Ir(ppy)_3$ (ppy=deprotonated 2-phenylpyridine) as emitter (Adachi, C.; et al. *Appl. Phys. Lett.* 77, 904 (2000)). An OLED emitting saturated red light based on the electrophosphorescent dopant Pt(OEP) ($H_2OEP$=octaethylporphyrin) has also been published and patented (Burrows, P.; et al. U.S. Pat. No. 6,048,630) but the maximum luminance is only around 500 Cd $m^{-2}$. A relevant patent is the use of the cyclometalated platinum(II) complex $Pt(thpy)_2$ (thpy=deprotonated 2-(2-thioenyl)pyridine) as dopant and PVK (poly(N-vinyl)carbazole) as host in a orange OLED (Lamansky, S.; et al. WO Pat. No. 00/57676). However, the Pt(II) complex used by the inventors was not stable for sublimation or vacuum deposition, thus a spin-casting method was applied, which led to higher driving voltages, quantum efficiency of 0.11% and luminance of 100 $Cd/m^2$ were obtained at 22 V.

SUMMARY OF THE INVENTION

The present invention is directed to novel organometallic light-emitting materials which may be used as electrophosphorescent emitters or dopants in high-performance OLEDs.

In particular, the present invention is directed to the design, synthesis, properties and applications of a family of phosphorescent emitters which, when added in effective amounts to suitable host material, including emissive compounds, electron transporting compounds and hole transporting compounds, tune the color of emission in the near-red range and enhance the device efficiency and brightness. Furthermore, the thermal stability of these phosphorescent emitters in the present invention are sufficient to allow sublimation, so that they may be readily incorporated into devices using vacuum deposition techniques, and hence high-performance electrophosphorescent devices prepared entirely from vacuum-deposited materials may be realized.

The family of electrophosphorescent emitters for use in the present invention are acetylide (alkynyl) complexes of the Group 10 metals, including platinum, with chemical structures of either Formula I or II:

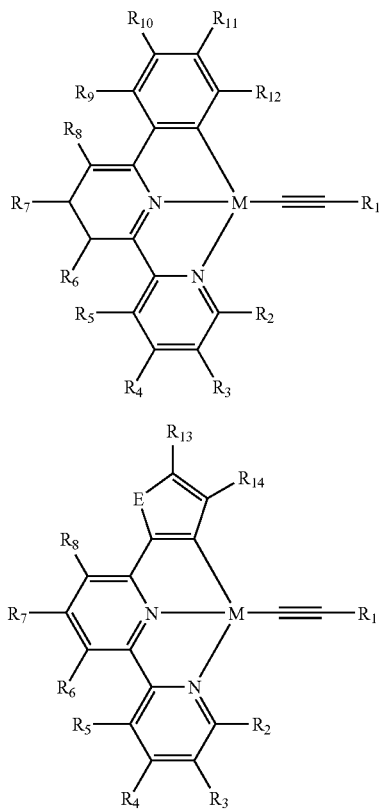

wherein E=Group 16 elements (including sulphur); M=Group 10 metal (including platinum); $R_1$–$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$ can also be selected from $(C\equiv C)_n R_{15}$, where ($C\equiv C$) represents a carbon-carbon triple bond (acetylide group), n is selected from 1 to 10, and $R_{15}$ is selected from alkyl, aryl, substituted aryl, and tri(alkyl)silyl. Group 16 elements are also known as the Group VIA elements. Group 10 elements also belong to Group VIIIB.

As established by thermogravimetric analysis, some of these complexes are thermally stable up to ~400° C. These complexes are good phosphorescent emitters and give strong orange to red emissions ($\lambda_{max}$ 550–630 nm) in fluid solutions by photo excitation and in OLEDs by electrical stimulation.

Generally, the present invention is directed to the syntheses and OLED applications of the family of electrophosphorescent emitters defined by Formula I and II. Our claims include the synthetic method for these novel complexes as well as their use as light-emitting material. These OLED applications include OLEDs wherein these complexes are incorporated as components either by vacuum deposition, spin-casting or other device fabrication methods.

In the present invention, the light-emitting material for use as an emitter or dopant in an OLED can comprise one or more metal-acetylide (metal-alkynyl) groups. In alternative, the light-emitting material for use as an emitter or dopant in an OLED comprises one or more platinum-acetylide (platinum-alkynyl) groups. In one embodiment, the light-emitting material for use as an emitter or dopant in an OLED can comprises a platinum atom coordinated by a tridentate ligand using one carbon and two nitrogen atoms. In another embodiment, the light-emitting material for use as an emitter or dopant in an OLED comprising a platinum atom coordinated by a tridentate ligand bearing a deprotonated phenyl carbonion and 2,2'-bipyridine.

In an exemplary embodiment, the light-emitting material for use as an emitter or dopant in an OLED can have a chemical structure represented by either Formula I or II:

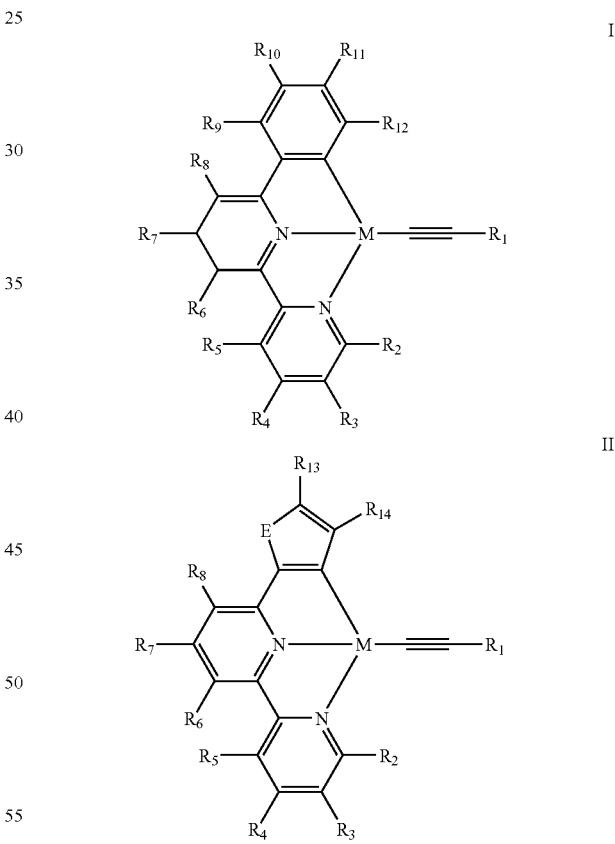

wherein E=Group 16 elements (including sulphur); M=Group 10 metal (including platinum); $R_1$–$R_{14}$ are each independently selected from the group consisting of hydrogen; halogen; alkyl; substituted alkyl; aryl; substituted aryl, with substituents selected from the group consisting of halogen, lower alkyl and recognized donor and acceptor groups. $R_1$ can also be selected from $(C\equiv C)_n R_{15}$, where ($C\equiv C$) represents a carbon-carbon triple bond (acetylide group), n is selected from 1 to 10, and $R_{15}$ is selected from alkyl, aryl, substituted aryl, and tri(alkyl)silyl.

In one embodiment, the light-emitting material can be deposited as a thin layer by sublimation or vacuum deposition. In another embodiment, the light-emitting material can be fabricated into OLEDs using spin-coating or other methods.

DETAILED DESCRIPTION OF THE INVENTION

Figure 1:
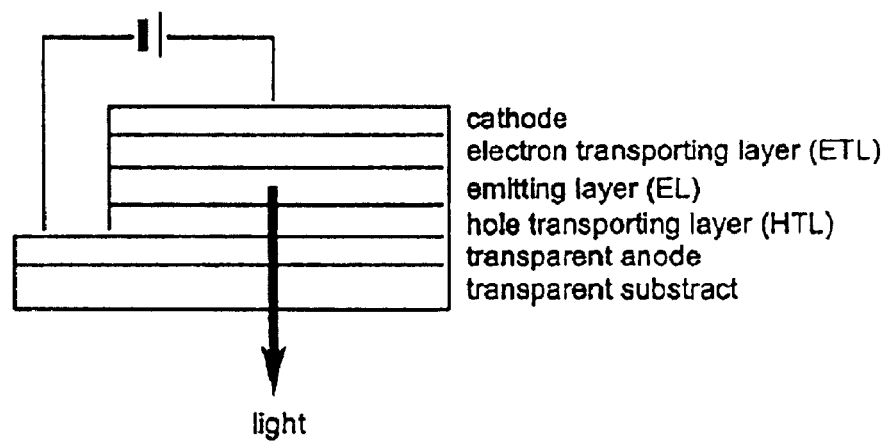
FIG. 1. General heterostructure of OLEDs.

The present invention is generally directed to syntheses and properties of a family of organometallic light-emitting materials and their applications in high-performance OLEDs. These novel complexes possess several chemical and structural characteristics as follows:

Cyclometalated diimine complexes of Group 10 metals, including platinum,

Neutral molecules,

Square planar coordination environment around metal,

Tridentate ligands defined as (C^N^AN) occupy three of the coordination sites, and Acetylide (alkynyl) group occupies the fourth coordination site.

The type of [(C^N^N)Pt(II)] complexes which combine the structural and spectroscopic characteristics of both diimine and cyclometalated Pt(II) complexes have been reported ((a) Lai, S. W.; et al. *Inorg. Chem.* 38, 4046 (1999). (b) Cheung, T. C.; et al. *J. Chem. Soc., Dalton Trans.* 1645 (1996). (c) Lai, S. W.; et al. *Organometallics* 18, 3327 (1999). (d) Yip, J. H. K.; et al. *Inorg. Chem.* 39, 3537 (2000). (e) Neve, F.; et al. *Inorg Chem.* 36, 6150 (1997)). The results demonstrated that these complexes are good room-temperature phosphorescent emitters both in solid state and in fluid solution. The relatively long-lived emissions occurring in the range of $\lambda_{max}$ 530–800 nm have been assigned to triplet metal-to-ligand charge transfer ($^3$MLCT) or metal-metal-to-ligand charge transfer ($^3$MMLCT) excited states.

The present invention will now be described in detail for specific preferred embodiment of the invention, it being understood that these embodiments are intended only a s illustrative examples and the invention is not to be limited thereto.

Syntheses of the complexes

We have synthesized a number of the tridentate cyclometalated Pt(II) arylacetylides

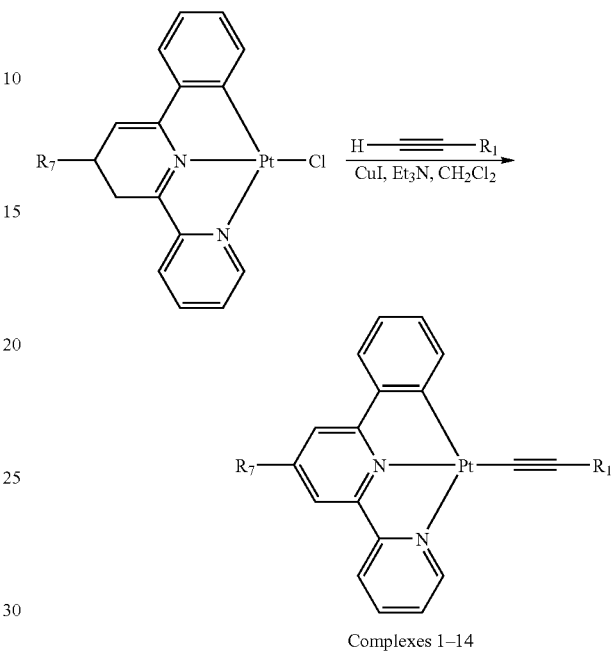

Complexes 1–14 with different substituents on the aryl rings which are depicted in either Formula I or II. The synthetic methods are shown in Scheme 1:

Scheme 1

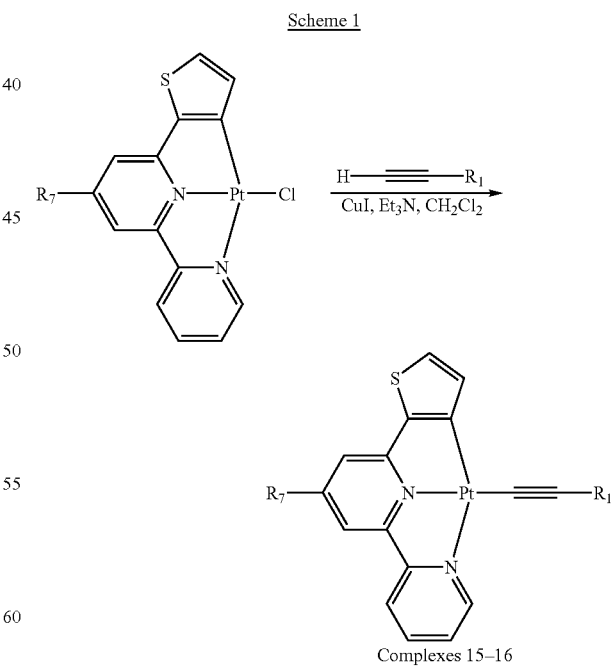

Complexes 15–16

The tridentate (C^N^N) ligands were prepared according to Kröhnke's method (Kröhnke, F. *Synthesis* 1 (1976)). The various acetylenes were prepared with Sonogashira's method (Takahashi, S. et al. *Synthesis* 627 (1980)). The Cl-ligated precursors [(C^N^N)PtCl] were prepared under Constable's condition (Constable, E. C.; et al. *J. Chem. Soc., Dalton Trans.* 2251 (1992) and 443 (1990)). The desired complexes were synthesized by Cu(I)-organic amine-catalyzed reactions. For example, to a mixture of [(C^N^N) PtCl] (0.33 mmol), terminal acetylene (1 mmol) and Et₃N (3 mL) in degassed CH₂Cl₂ (30 mL) solution was added CuI (5 mg). The suspension was stirred for 12 h under a nitrogen atmosphere at room temperature and in the absence of light. The resultant mixture was rotatory-evaporated to dryness. The crude product was purified by flash chromatography (neutral Al₂O₃, CH₂Cl₂ as eluent) and/or recrystallization from dichloromethane/diethyl ether. Examples are listed in Table I but not limited by them:

TABLE I

| Complex | Chemical Structure | Characterization Data |
|---|---|---|
| 1 | 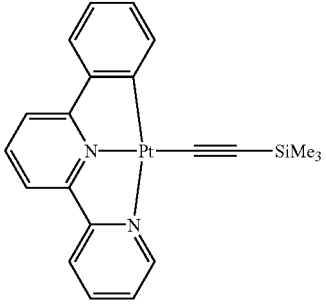 | orange crystalline powder. FAB MS: 524 (M⁺ + H), 523 (M⁺); ¹H NMR (300 MHz, CDCl₃, 22° C., TMS): δ 9.02 (d, 1H, J = 5.3 Hz), 7.94 (t, 1H, J = 7.8 Hz), 7.87 (d, 1H, J = 7.4 Hz), 7.82 (d, 1H, J = 8.0 Hz), 7.68 (t, 1H, J = 8.0 Hz), 7.51 (d, 1H, J = 7.7 Hz), 7.45 (t, 1H, J = 7.5 Hz), 7.41 (d, 1H, J = 8.1 Hz), 7.21 (d, 1H, J = 7.2 Hz), 7.15 (t, 1H, J = 7.4 Hz), 7.02 (t, 1H, J = 7.5 Hz), 0.27 (s, 9H). |
| 2 | 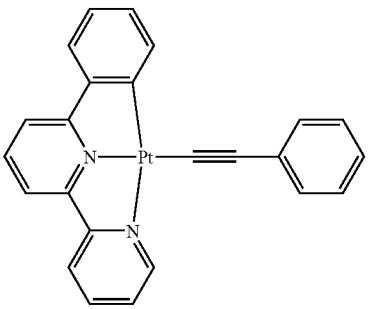 | orange crystalline powder. FAB MS: 528 (M⁺ + H), 527 (M⁺); ¹H NMR (300 MHz, CDCl₃, 22° C., TMS): δ = 9.15 (d, 1H, J = 4.3 Hz), 7.97 (m, 2H), 7.85 (d, 1H, J = 8.1 Hz), 7.75 (t, 1H, J = 8.0 Hz), 7.55 (m, 3H), 7.48 (m, 2H), 7.31 (m, 3H), 7.17 (t, 2H, J = 7.0 Hz), 7.05 (t, 1H, J = 7.4 Hz). |
| 3 | 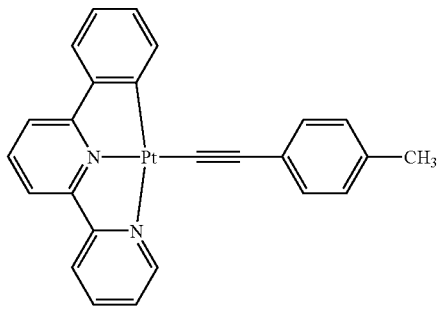 | orange-red crystalline powder. FAB MS: 542 (M⁺ + H), 541 (M⁺); ¹H NMR (300 MHz, CDCl₃, 22° C., TMS): δ = 9.07 (d, 1H, J = 4.3 Hz), 7.92 (m, 2H), 7.82 (d, 1H, J = 7.8 Hz), 7.69 (t, 1H, J = 8.0 Hz), 7.53 (d, 1H, J = 7.3 Hz), 7.43 (m, 4H), 7.27 (d, 1H, J = 6.3 Hz), 7.15 (t, 1H, J = 7.3 Hz), 7.10 (d, 2H, J = 7.9 Hz), 7.02 (t, 1H, J = 7.5 Hz), 2.35 (s, 3H). |
| 4 | 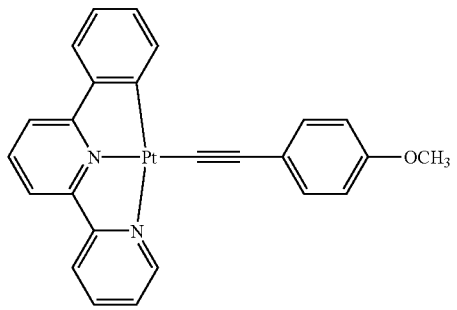 | red crystalline powder. FAB MS: 558 (M⁺ + H), 557 (M⁺); ¹H NMR (300 MHz, CDCl₃, 22° C., TMS): δ = 9.12 (d, 1H, J = 5.2 Hz), 7.95 (m, 2H), 7.83 (d, 1H, J = 7.9 Hz), 7.72 (t, 1H, J = 8.0 Hz), 7.50 (m, 3H), 7.49 (d, 2H, J = 8.8 Hz), 7.30 (d, 1H, J = 6.6 Hz), 7.16 (t, 1H, J = 7.4 Hz), 7.03 (t, 2H, J = 7.4 Hz), 6.84 (d, 2H, J = 8.8 Hz), 3.82 (s, 3H). |

TABLE I-continued

| Complex | Chemical Structure | Characterization Data |
|---|---|---|
| 5 | [Pt(terpy)(C≡C-C6H4-Cl)] | orange-red crystalline powder. FAB MS: 562 (M+); $^1$H NMR (300 MHz, CDCl$_3$, 22° C., TMS): δ = 9.05 (d, 1H, J = 5.1 Hz), 7.94 (t, 1H, J = 7.8 Hz), 7.87 (d, 1H, J = 7.5 Hz), 7.81 (d, 1H, J = 7.9 Hz), 7.71 (t, 1H, J = 8.0 Hz), 7.52 (d, 1H, J = 7.7 Hz), 7.46 (m, 2H), 7.45 (d, 1H, J = 8.5 Hz), 7.27 (d, 1H, J = 4.2 Hz), 7.23 (d, 2H, J = 8.8 Hz), 7.15 (t, 1H, J = 7.4 Hz), 7.03 (t, 1H, J = 7.4 Hz). |
| 6 | [Pt(terpy)(C≡C-C6H4-F)] | black-red crystals. FAB MS: 546 (M+ + H), 545 (M+); $^1$H NMR (300 MHz, CDCl$_3$, 22° C., TMS): δ 9.12 (d, 1H, J = 5.2 Hz), 7.97 (t, 1H, J = 7.9 Hz), 7.92 (d, 1H, J = 7.6 Hz), 7.84 (d, 1H, J = 8.0 Hz), 7.74 (t, 1H, J = 8.0 Hz), 7.56–7.47 (m, 5H), 7.32 (d, 1H, J = 7.6 Hz), 7.17 (t, 1H, J = 7.4 Hz), 7.05 (t, 1H, J = 7.5 Hz), 6.98 (pseudo-t, 2H, J = 7.7 Hz). |
| 7 | [Pt(terpy)(C≡C-C6H4-NO2)] | orange crystalline powder. FAB MS: 573 (M+ + H), 572 (M+); $^1$H NMR (300 MHz, d$_6$-DMSO, 22° C., TMS): δ = 8.98 (d, 1H, J = 4.5 Hz), 8.48 (d, 1H, J = 8.0 Hz), 8.32 (t, 1H, J = 8.0 Hz), 8.20 (d, 1H, J = 7.4 Hz), 8.14 (d, 2H, J = 8.8 Hz), 8.11 (t, 1H, J = 8.0 Hz), 7.99 (d, 1H, J = 7.8Hz), 7.83 (t, 1H, J = 7.5 Hz), 7.68 (d, 1H, J = 7.3 Hz), 7.62 (d, 1H, J = 7.4 Hz), 7.58 (d, 2H, J = 8.9 Hz), 7.11 (t, 1H, J = 7.3 Hz), 7.05 (t, 1H, J = 7.3 Hz). |
| 8 | [Pt(terpy)(C≡C-thiophene)] | brown crystals. FAB MS: 534 (M+ + H), 533 (M+); $^1$H NMR (300 MHz, d$_6$-DMSO, 22° C., TMS): δ = 8.94 (d, 1H, J = 5.1 Hz), 8.46 (d, 1H, J = 7.9 Hz), 8.30 (t, 1H, J = 7.8 Hz), 8.17 (d, 1H, J = 7.6 Hz), 8.08 (t, 2H, J = 7.9 Hz), 7.96 (d, 1H, J = 7.9 Hz), 7.84 (t, 1H, J = 6.4 Hz), 7.66 (d, 1H, J = 6.2 Hz), 7.59 (d, 1H, J = 7.4 Hz), 7.21 (d, 1H, J = 4.9 Hz), 7.10 (t, 1H, J = 7.3 Hz), 7.03 (t, 1H, J = 7.3 Hz), 6.97–6.92 (m, 2H). |

TABLE I-continued

| Complex | Chemical Structure | Characterization Data |
|---|---|---|
| 9 | 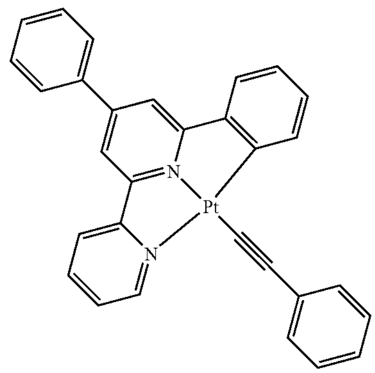 | orange crystalline powder. FAB MS: 604 (M⁺ + H), 603 (M⁺); $^1$H NMR (300 MHz, d$_6$-DMSO, 22° C., TMS): δ = 8.99 (d, 1H, J = 4.8 Hz), 8.68 (d, 1H, J = 8.0 Hz), 8.50 (s, 1H), 8.32 (t, 1H, J = 7.7 Hz), 8.24 (s, 1H), 8.08–8.05 (m, 2H), 7.84–7.78 (m, 2H), 7.70 (d, 1H, J = 7.9 Hz), 7.61–7.55 (m, 3H), 7.36 (d, 1H, J = 7.2 Hz), 7.26 (t, 1H, J = 7.6 Hz), 7.17–7.01 (m, 3H). |
| 10 | 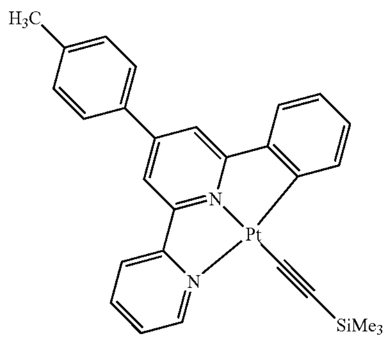 | orange crystalline powder. FAB MS: 614 (M⁺ + H), 613 (M⁺); $^1$H NMR (300 MHz, CDCl$_3$, 22° C., TMS): δ =8.90 (d, 1H, J = 5.4 Hz), 7.99 (t, 1H, J = 7.5 Hz), 7.90 (d, 1H, J = 8.0 Hz), 7.76 (d, 1H, J = 6.2 Hz), 7.60–7.57 (m, 3H), 7.40–7.31 (m, 4H), 7.26 (d, 1H, J = 6.1 Hz), 7.03–6.98 (m, 2H), 2.48 (s, 3H), 0.33 (s, 9H). |
| 11 | 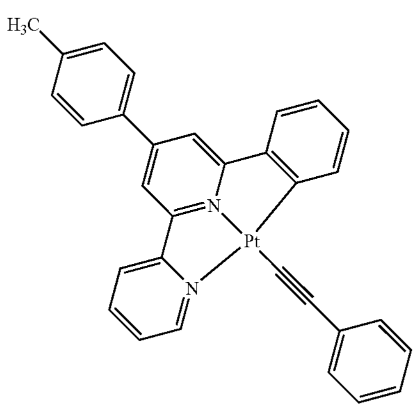 | orange crystalline powder. FAB MS: 618 (M⁺ + H), 617 (M⁺); $^1$H NMR (300 MHz, d$_6$-DMSO, 22° C., TMS): δ = 9.04 (d, 1H, J = 5.0 Hz), 8.69 (d, 1H, J = 7.9 Hz), 8.50 (s, 1H), 8.34 (t, 1H, J = 7.7 Hz), 8.24 (s, 1H), 8.01 (d, 2H, J = 7.5 Hz), 7.84–7.74 (m, 3H), 7.40–7.30 (m, 4H), 7.30 (t, 2H, J = 7.5 Hz), 7.18–7.06 (m, 3H), 2.40 (s, 3H). |
| 12 | 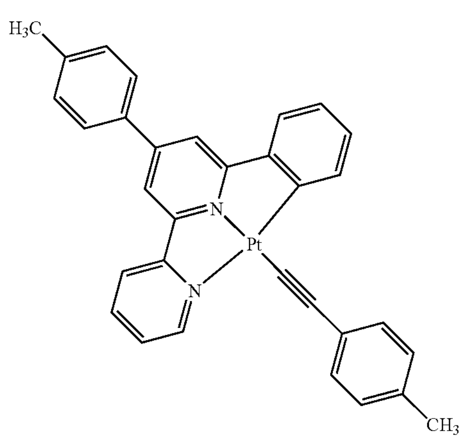 | red crystals. FAB MS: 632 (M⁺ + H), 631 (M⁺); $^1$H NMR (300 MHz, d$_6$-DMSO, 22° C., TMS): δ = 9.05 (d, 1H, J = 4.9 Hz), 8.56 (d, 1H, J = 8.0 Hz), 8.34 (s, 1H), 8.20 (t, 1H, J = 7.9 Hz), 8.00 (s, 1H), 7.85 (d, 2H, J = 8.1 Hz), 7.76–7.68 (m, 2H), 7.62 (d, 1H, J = 8.2 Hz), 7.31 (d, 2H, J = 8.1 Hz), 7.25 (d, 2H, J = 8.0 Hz), 7.07–6.97 (m, 4H), 2.39 (s, 3H), 2.28 (s, 3H). |

TABLE I-continued

| Complex | Chemical Structure | Characterization Data |
|---|---|---|
| 13 | 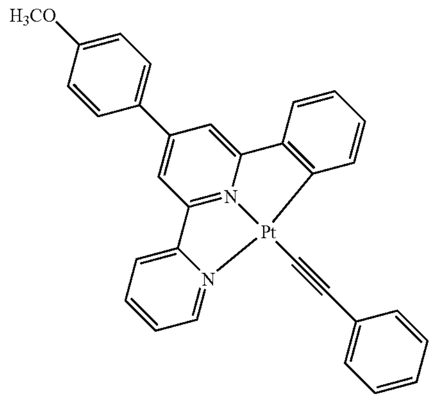 | orange crystalline powder. FAB MS: 634 (M⁺ + H), 633 (M⁺); $^1$H NMR (300 MHz, d$_6$-DMSO, 22° C., TMS): δ =9.00 (d, 1H, J = 4.9 Hz), 8.69 (d, 1H, J = 8.1 Hz), 8.48 (s, 1H), 8.32 (t, 1H, J = 7.9 Hz), 8.26 (s, 1H), 8.08 (d, 2H, J = 8.8 Hz), 8.06–7.81 (m, 2H), 7.72 (d, 1H, J = 7.1 Hz), 7.35 (d, 2H, 17.1 Hz), 7.26 (t, 2H, J = 7.6 Hz), 7.16–7.04 (m, 5H), 3.84 (s, 3H). |
| 14 | 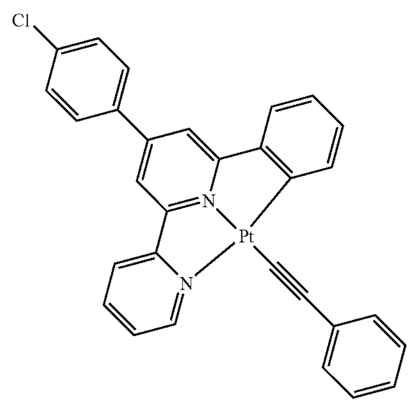 | brown crystalline powder. FAB MS: 638 (M⁺); $^1$H NMR (300 MHz, d$_6$-DMSO, 22° C., TMS): δ = 8.99 (broad, 1H), 8.64 (d, 1H, J = 7.7 Hz), 8.47 (s, 1H), 8.31 (t, 1H, J = 7.6 Hz), 8.21 (s, 1H), 8.09 (d, 2H, J = 8.1 Hz), 7.82–7.68 (m, 3H), 7.62 (d, 2H, J = 8.2 Hz), 7.38 (d, 2H, J = 7.2 Hz), 7.28 (t, 2H, J = 7.3 Hz), 7.18 (t, 1H, J = 7.0 Hz), 7.08–7.03 (m, 2H). |
| 15 | 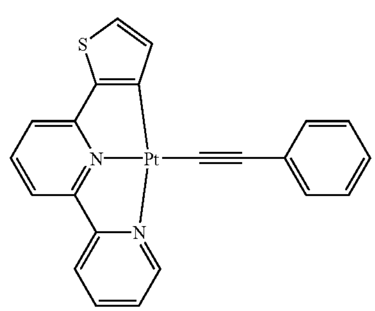 | brown needles. FAB MS: 534 (M⁺ + H), 533 (M⁺); $^1$H NMR (300 MHz, d$_6$-DMSO, 22° C., TMS): δ = 9.01 (d, 1H, J = 5.0 Hz), 8.46 (d, 1H, J = 8.2 Hz), 8.35 (t, 1H, J = 7.9 Hz), 8.02 (d, 1H, J = 7.6 Hz), 7.96 (t, 1H, J = 7.8 Hz), 7.85 (t, 1H, J = 6.4 Hz), 7.72 (d, 1H, J = 4.9 Hz), 7.56 (d, 1H, J = 7.3 Hz), 7.38 (d, 2H, J = 7.0 Hz), 7.29 (t, 2H, J = 7.6 Hz), 7.17 (t, 1H, J = 7.3 Hz), 7.11 (d, 1H, J = 4.6 Hz). |
| 16 | 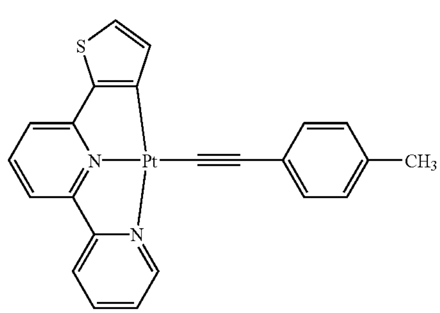 | brown needles. FAB MS: 548 (M⁺ + H), 547 (M⁺); $^1$H NMR (300 MHz, d$_6$-DMSO, 22° C., TMS): δ =9.03 (d, 1H, J = 5.2 Hz), 8.47 (d, 1H, J = 8.2 Hz), 8.34 (t, 1H, J = 7.2 Hz), 8.02 (d, 1H, J = 7.9 Hz), 7.96 (t, 1H, J = 7.7 Hz), 7.86 (t, 1H, J = 6.3 Hz), 7.73 (d, 1H, 4.9 Hz), 7.56 (d, 1H, J = 7.6 Hz), 7.26 (d, 2H, J = 7.9 Hz), 7.13 (d, 1H, J = 4.6 Hz), 7.11 (d, 2H, J = 7.9 Hz), 2.30 (s, 3H). |

Thermal-stability of the Complexes

Figure 2:
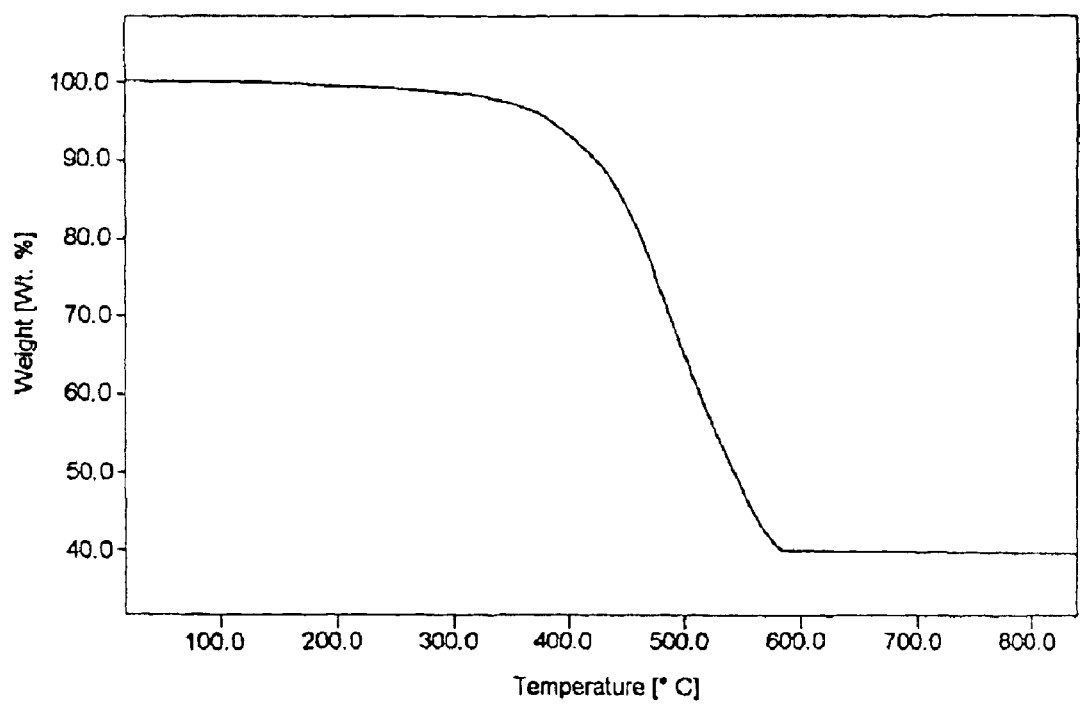
FIG. 2. TGA curve of complex 2.
Figure 3:
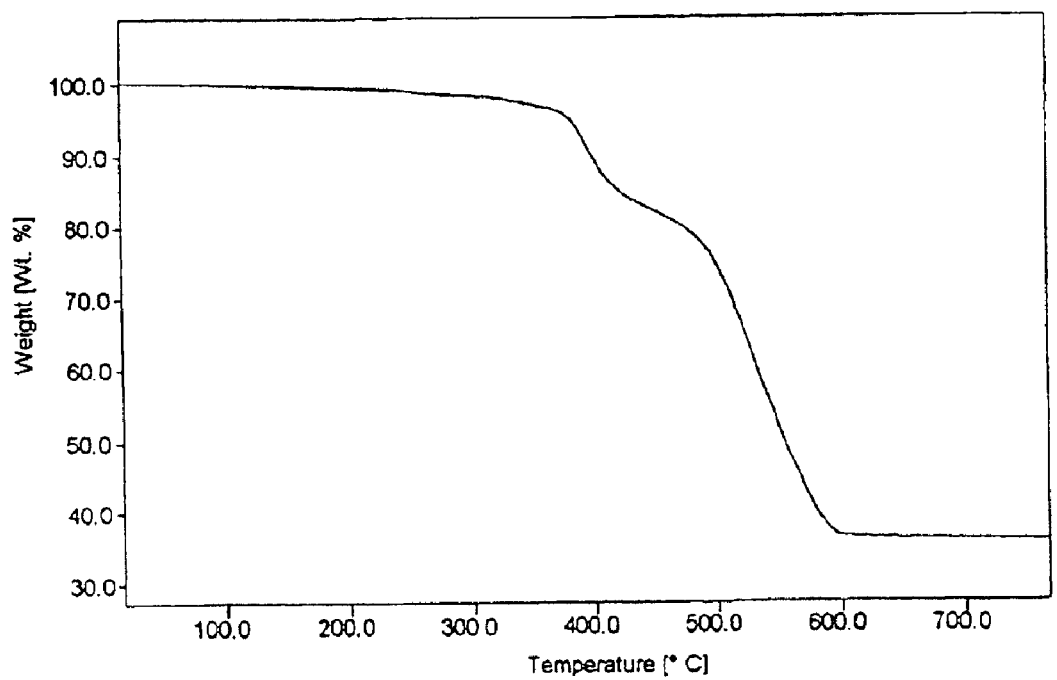
FIG. 3. TGA curve of complex 15.

Ideally, a low molecular weight component to be used in OLEDs should be sublimable and stable at standard deposition conditions. Importantly, many of the complexes in the present invention are thermally stable up to ~400° C. and decompose to give metallic platinum only at temperature above 420° C. (see TGA curves for complexes 2 and 15 in FIGS. 2 and 3 respectively).

The observed thermal stability of these complexes described in the present invention which contain a tridentate cyclometalating ligand, contrasts sharply with the bidentate Pt(thpy)$_2$ emitter described by Lamasky et al. which are unstable upon sublimation.

Spectroscopic Properties of the Complexes

In present invention, the ligation of an acetylide group to the (C^N^N)Pt(II) moiety neutralizes the positive charge centered on Pt(II), enhances the stability of these complexes, and moreover, shifts the $^3$MLCT emission bathochromically. The family of complexes depicted by Formula I and II display strong orange to red photoluminescence in fluid solution. Examples of characteristic absorption and emission band of these emitters in present invention are summarized in Table II:

TABLE II

| Complex (see Table I) | Absorption MLCT Band/nm ($\epsilon$/mol dm$^{-1}$ cm$^{-1}$) | Emission $\lambda_{max}$/nm ($\tau_0$/µs; $\phi_0$) |
| --- | --- | --- |
| 1 | 427 (5490), 450 (sh, 4920), 505 (sh, 430) | 570 (0.31; 0.041) |
| 2 | 434 (5180), 455 (4940), 510 (sh, 470) | 582 (0.39; 0.037) |
| 3 | 440 (5090), 465 (sh, 4950), 515 (sh, 1190) | 600 (0.17; 0.019) |
| 4 | 440 (4200), 460 (sh, 4220), 520 (sh, 1570) | 630 |
| 5 | 432 (8670), 455 (sh, 8310), 515 (sh, 720) | 598 (0.53; 0.076) |
| 6 | 433 (4880), 453 (sh, 4760), 515 (sh, 640) | 585 (0.33; 0.033) |
| 7 | 415 (sh, 12930), 510 (sh, 540) | 560 (0.93; 0.077) |
| 15 | 436 (4970), 460 (sh, 4490), 515 (sh, 460) | 615 (1.02; 0.029), 660 (sh) |
| 16 | 442 (5010), 465 (sh, 4800), 520 (sh, 670) | 616 (0.91; 0.025), 660 (sh) |

Figure 4:
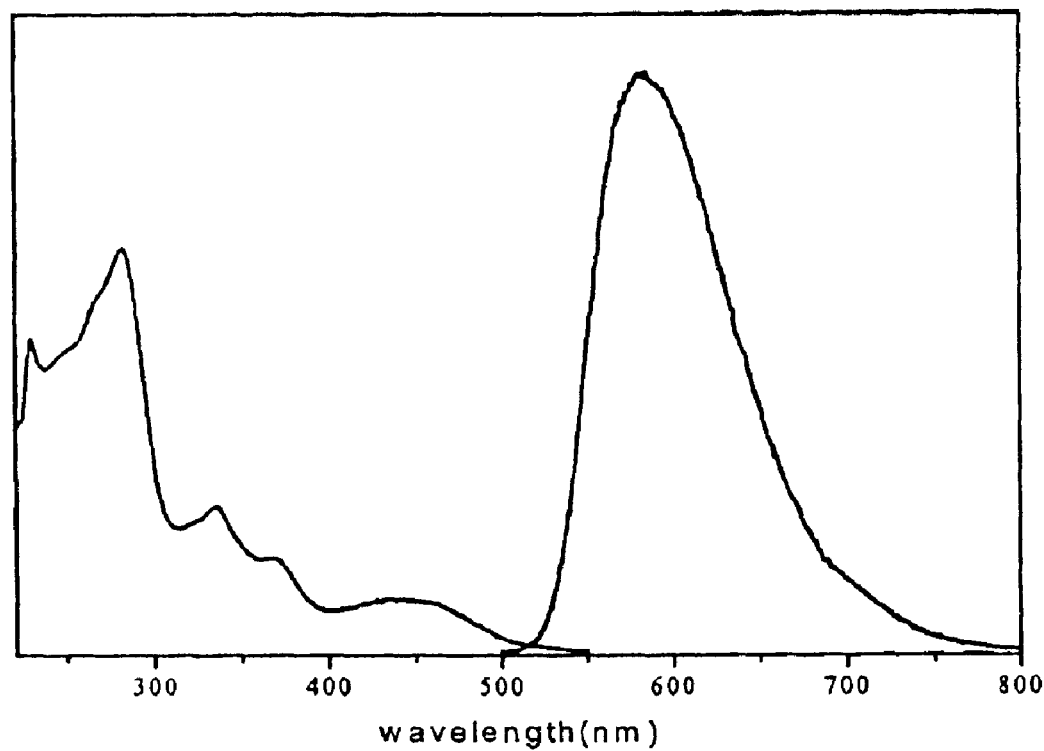
FIG. 4. UV-vis absorption and emission spectra of complex 2 in $CH_2Cl_2$ at 298 K.
Figure 5:
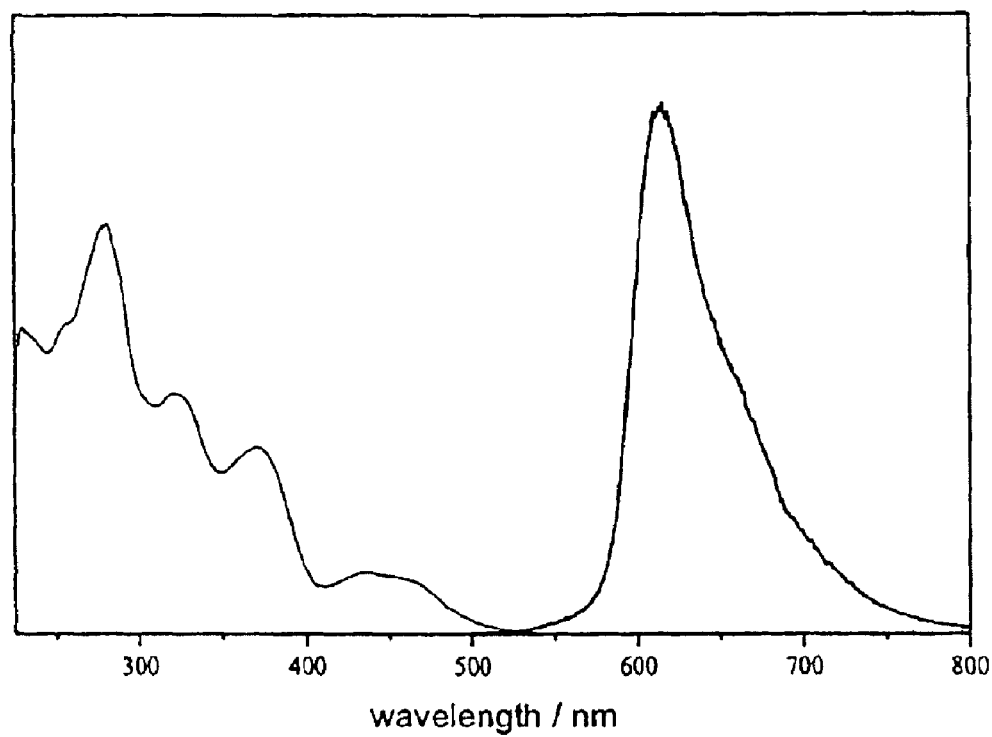
FIG. 5. UV-vis absorption and emission spectra of complex 15 in $CH_2Cl_2$ at 298 K.

Notice that all the data were collected with degassed CH$_2$Cl$_2$ solution at 298 K. Exemplified absorption and emission spectra for complexes 2 and 15 are shown in FIGS. 4 and 5 respectively. The intense orange to red phosphorescence of the complexes in the present invention together with their stability towards sublimation means that these materials can be used as emitters or dopants in high-performance OLEDs.

Organic Light-emitting Devices

Figure 6:
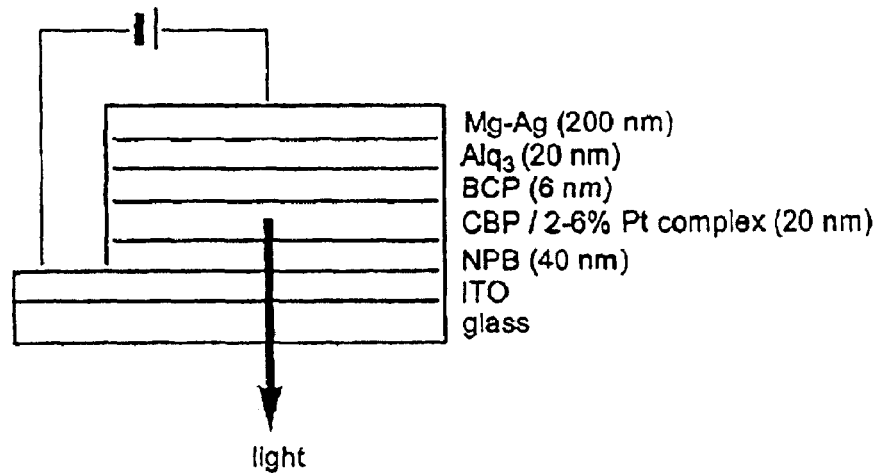
FIG. 6. The heterostructure of OLEDs in present invention.

The devices using the complexes in present invention, as fabricated by Prof. S. T. Lee of City University of Hong Kong, possess the multi-layer heterostructure shown in FIG. 6.

All the organic layers including the Pt complexes described above and cathodes were vacuum-deposited onto the ITO subtrate. NPB (N,N'-di-1-naphthyl-N,N'-diphenyl-benzidine) and Alq$_3$ (q=8-hydroxyquinolinyl) were used as the hole transporting and electron transporting layer, respectively. BCP (2,9-dimethyl-4,7-diphenyl-1,10-phenanthroline, bathocuproine) was used to confine excitons within the luminescent zone. Magnesium silver alloy was applied as the cathode. The selected Pt complex was doped into the conductive host material CBP (4,4'-N,N'-dicarbazole-biphenyl) as phosphorescent emitter. The optimal doping levels were adjusted at 2, 4 and 6% and electroluminescence from the Pt complexes were observed.

EXAMPLES

A number of examples are listed below to further illustrate the invention

Example 1

Figure 7:
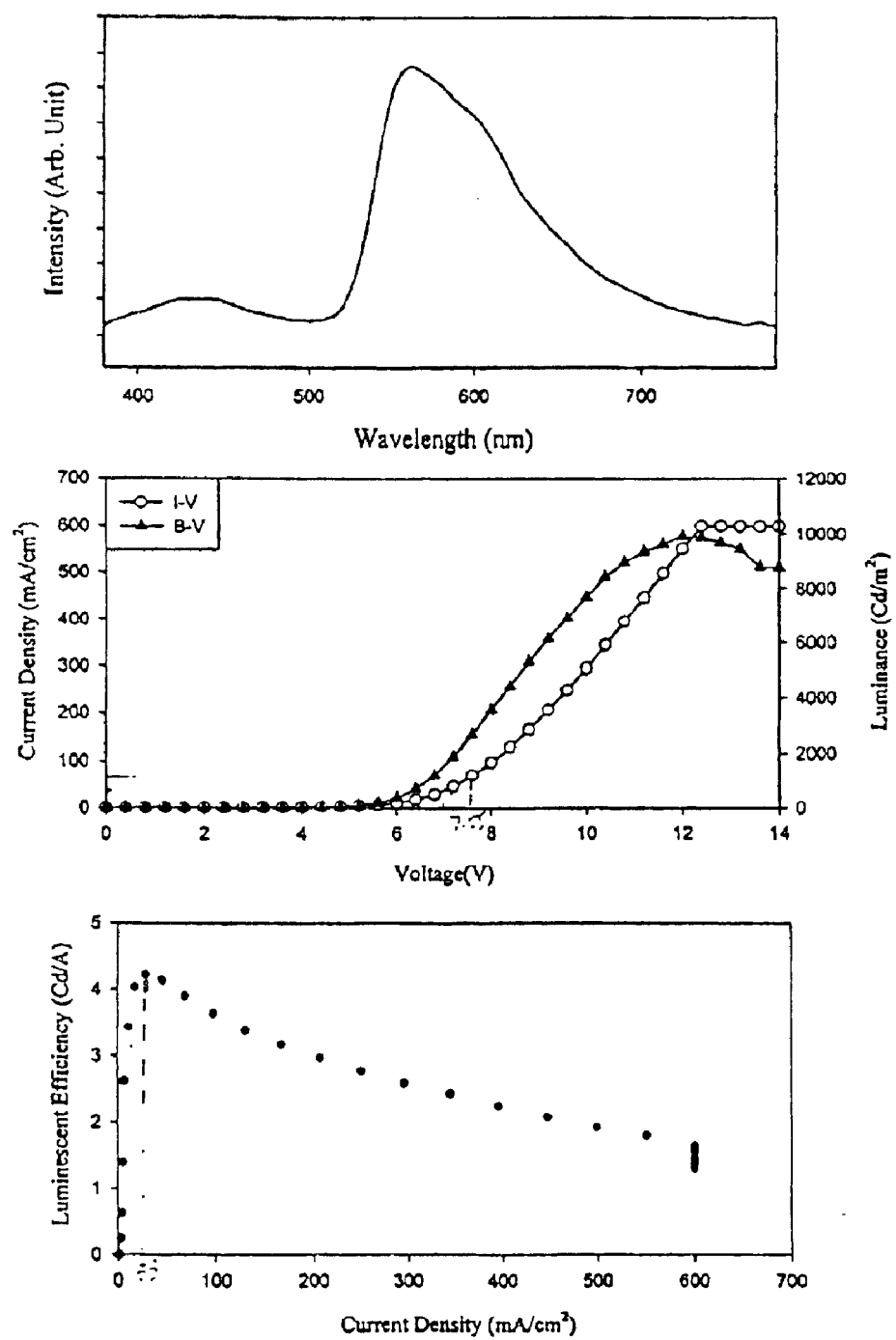
FIG. 7. Electroluminescent spectrum, current-voltage (I-V) and luminance-voltage (B-V) curves and luminescent efficiency-current density curve of the device using complex 2 as emitter with a doping level of 2%.

Complex 2 was used as the emitter. Typical electroluminescent spectrum, current-voltage (I-V) and luminance-voltage (B-V) curves and luminescent efficiency-current density curve of the device with a doping level of 2% are shown in FIG. 7. Turn-on voltage: ~5 V; maximum luminance: 9600 Cd/m$^2$ at 12 V; maximum efficiency: 4.2 Cd/A at 25 mA/cm$^2$. In the electroluminescent spectrum, a peak at 430 nm besides the band at 560–630 nm is observed, indicating insufficient energy transfer between the host and the dopant.

Example 2

Figure 8:
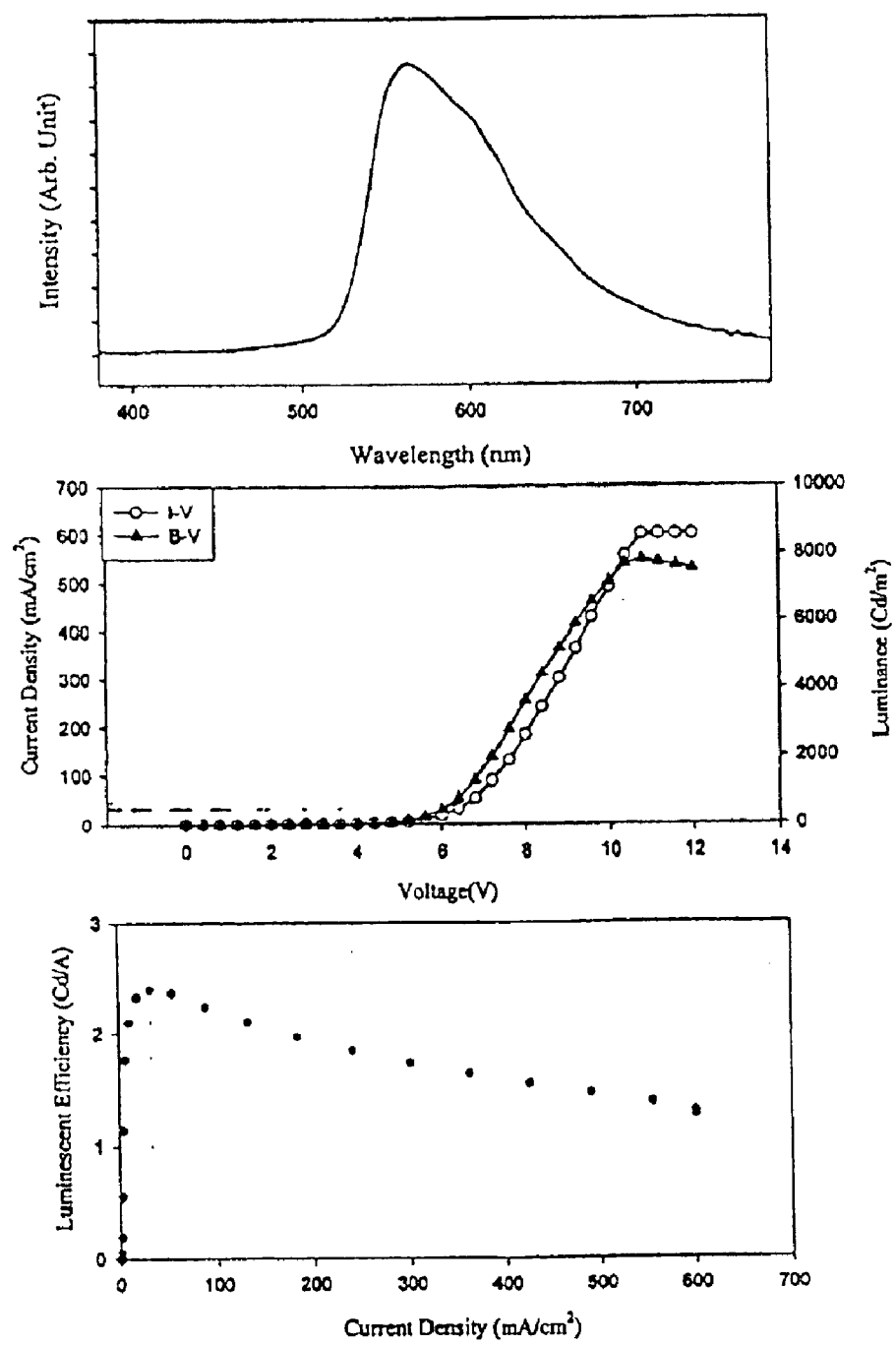
FIG. 8. Electroluminescent spectrum, current-voltage (I-V) and luminance-voltage (B-V) curves and luminescent efficiency-current density curve of the device using complex 2 as emitter with a doping level of 4%.

The performance of the device using complex 2 as emitter with a doping level of 4% are shown in FIG. 8. Turn-on voltage: ~5 V; maximum luminance: 7900 Cd/m$^2$ at 10 V; maximum efficiency: 2.4 Cd/A at 30 mA/cm$^2$. At this doping level, energy transfer between the host and the dopant is saturated, thus emission from the host is avoided.

Example 3

Figure 9:
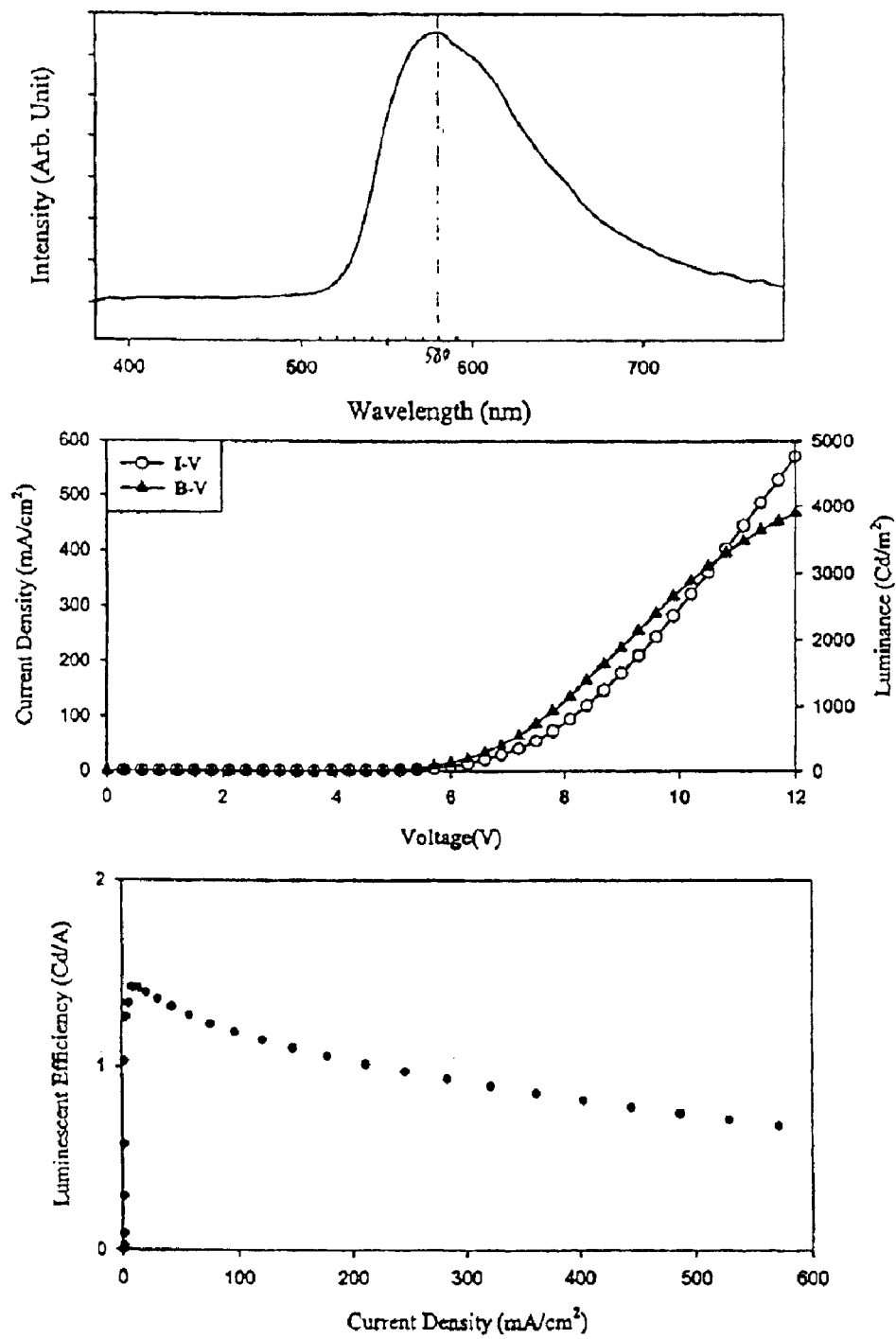
FIG. 9. Electroluminescent spectrum, current-voltage (I-V) and luminance-voltage (B-V) curves and luminescent efficiency-current density curve of the device using complex 3 as emitter with a doping level of 4%.

Complex 3 was used as the emitter. The performance of the device with a doping level of 4% are shown in FIG. 9. A bathochromic electroluminescence is observed ($\lambda_{max}$ 580 nm), which is coinciding with the trend of the photoluminescence shown by these complexes in room-temperature CH$_2$Cl$_2$ solutions. Turn-on voltage: ~5 V; maximum luminance: 4000 Cd/m$^2$ at 12 V; maximum efficiency: 1.4 Cd/A at 20 mA/cm$^2$.

Example 4

Figure 10:
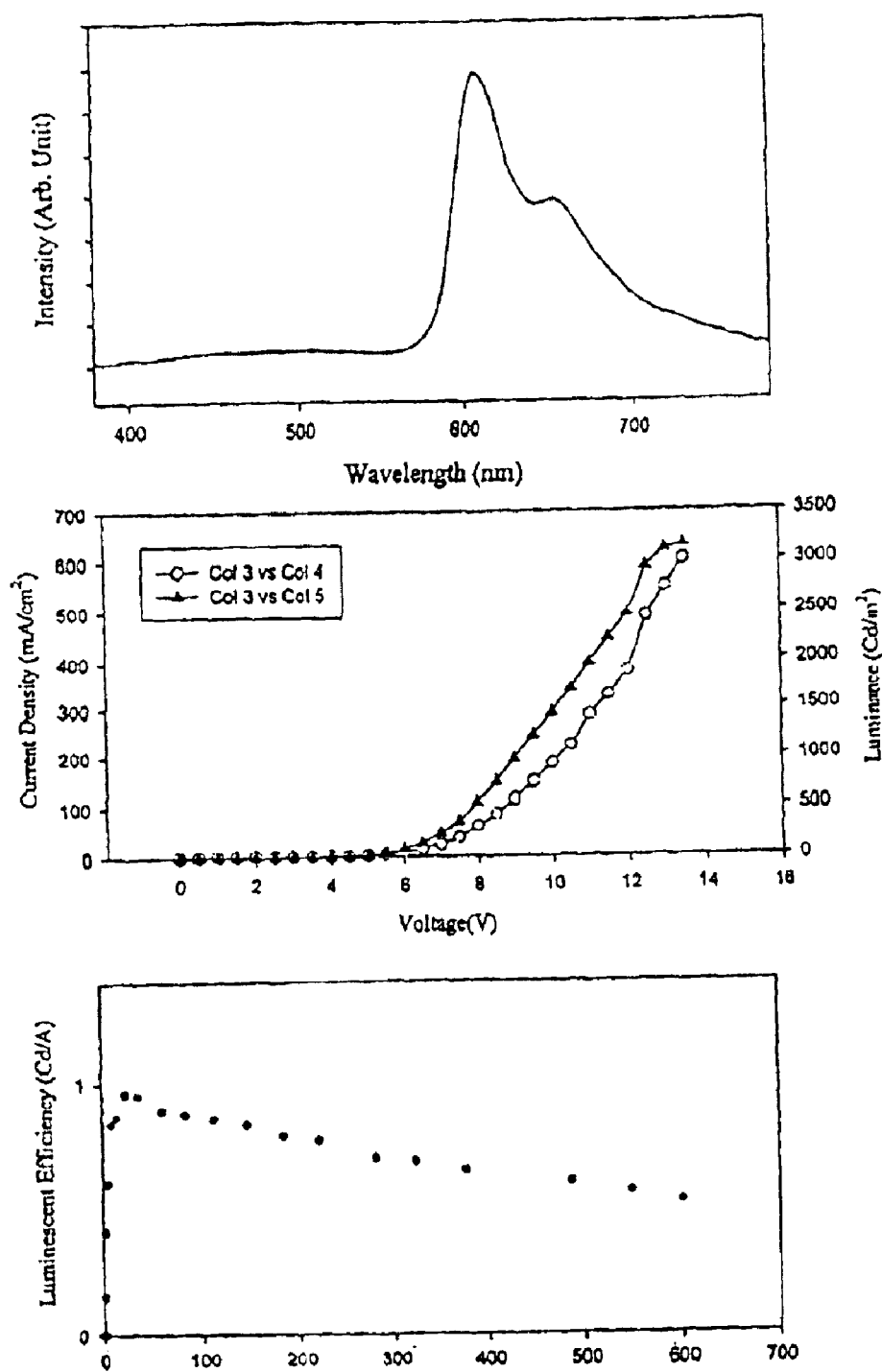
FIG. 10. Electroluminescent spectrum, current-voltage (I-V) and luminance-voltage (B-V) curves and luminescent efficiency-current density curve of the device using complex 16 as emitter with a doping level of 4%.

Complex 16 was used as the emitter. The performance of the device with a doping level of 4% are shown in FIG. 10. The electroluminescence is red with vibronically structured emission spectrum ($\lambda_{max}$ 610 nm, 660 nm). Turn-on voltage: ~5 V; maximum luminance: 3200 Cd/m$^2$ at 13 V; maximum efficiency: 1.0 Cd/A at 30 mA/cm$^2$.

Generally, the organometallic light-emitting materials as depicted in Figures I and II in present invention are demonstrated to be novel electrophosphorescent emitters applicable to high-efficiency and -brightness orange to red light OLEDs.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A light-emitting material for use as an emitter or dopant in an organic light-emitting diode having a chemical structure

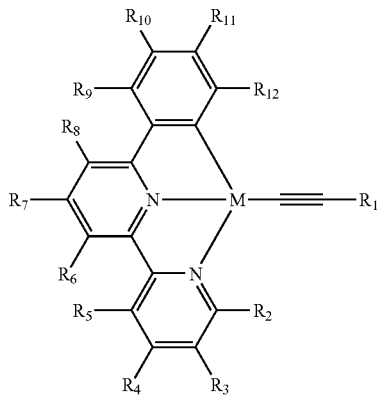

I

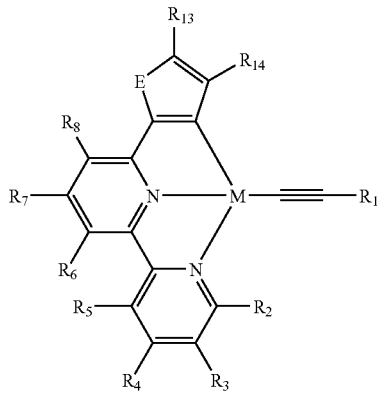

II represented by either Formula I or II:
wherein E=Group 16 element; M=Group 10 metal; $R_{1-14}$ are each independently selected from the group consisting of hydrogen; halogen; alkyl; substituted alkyl; aryl; substituted aryl.

2. The light-emitting material in accordance with claim 1 which can be deposited as a thin layer by sublimation or vacuum deposition.

3. The light-emitting material in accordance with claim 1 which can be fabricated into organic light-emitting diodes using spin-coating or other methods.

4. The light-emitting material in accordance with claim 1, wherein E is sulphur.

5. The light-emitting material in accordance with claim 1, wherein M is platinum.

* * * * *